United States Patent
Arellano et al.

(10) Patent No.: US 11,715,868 B2
(45) Date of Patent: Aug. 1, 2023

(54) ELECTROCHEMICAL CELL CASING HAVING AN ELECTROLYTE FILL PORT WITH AN EMBOSSED RIM LID DESIGN

(71) Applicant: Greatbatch Ltd., Clarence, NY (US)

(72) Inventors: Jared D. Arellano, Akron, NY (US); Lasantha Viyannalage, Pittsford, NY (US)

(73) Assignee: Greatbatch Ltd., Clarence, NY (US)

( * ) Notice: Subject to any disclaimer, the term of this patent is extended or adjusted under 35 U.S.C. 154(b) by 13 days.

(21) Appl. No.: 17/471,686

(22) Filed: Sep. 10, 2021

(65) Prior Publication Data

US 2022/0085473 A1 Mar. 17, 2022

Related U.S. Application Data

(60) Provisional application No. 63/076,963, filed on Sep. 11, 2020.

(51) Int. Cl.
*H01M 50/645* (2021.01)
*H01M 50/188* (2021.01)

(52) U.S. Cl.
CPC ....... *H01M 50/645* (2021.01); *H01M 50/188* (2021.01)

(58) Field of Classification Search
CPC ............. H01M 50/645; H01M 50/188; H01M 50/119; H01M 10/0427; H01M 50/159; H01M 50/636; H01M 50/109; H01M 50/153; H01M 50/169; H01M 50/191; Y02E 60/10; Y02P 70/50; A61N 1/378
See application file for complete search history.

(56) References Cited

U.S. PATENT DOCUMENTS

| | | | |
|---|---|---|---|
| 5,415,959 A | 5/1995 | Pyszczek et al. | |
| 6,610,443 B2 | 8/2003 | Paulot et al. | |
| 7,128,765 B2 | 10/2006 | Paulot et al. | |
| 10,446,825 B2 | 10/2019 | Voss et al. | |
| 10,957,884 B1 | 3/2021 | Dianetti et al. | |
| 2006/0037190 A1* | 2/2006 | Rubino | H01M 50/186 29/623.2 |
| 2011/0097623 A1 | 4/2011 | Marinis et al. | |
| 2021/0143484 A1* | 5/2021 | Chen | H01M 50/109 |

FOREIGN PATENT DOCUMENTS

| | | |
|---|---|---|
| EP | 1441400 A1 | 7/2004 |
| EP | 3926740 A1 | 12/2021 |

OTHER PUBLICATIONS

"Extended European Search Report, Application No. 21196416.8, dated Jan. 26, 2022".

* cited by examiner

*Primary Examiner* — Niki Bakhtiari
*Assistant Examiner* — Bartholomew A Hornsby
(74) *Attorney, Agent, or Firm* — Michael F. Scalise

(57) ABSTRACT

A miniature electrochemical cell of a primary or secondary chemistry with a total volume that is less than 0.5 cc is described. The cell has a casing comprising an annular sidewall supported on a lower plate opposite an upper lid. The lid has a sealed electrolyte fill port that is axially aligned with an annulus residing between the inner surface of the annular sidewall and the electrode assembly. The fill port axially aligned with the annulus between the electrode assembly and the casing sidewall allows the casing to be filled with electrolyte using a vacuum filling process so that activating electrolyte readily wets the anode and cathode active materials and the intermediate separator.

22 Claims, 3 Drawing Sheets

ELECTROCHEMICAL CELL CASING HAVING AN ELECTROLYTE FILL PORT WITH AN EMBOSSED RIM LID DESIGN

CROSS-REFERENCE TO RELATED APPLICATION

This application claims priority to U.S. provisional application Ser. No. 63/076,963, filed on Sep. 11, 2020.

BACKGROUND OF THE INVENTION

1. Field of the Invention

The present invention relates to the conversion of chemical energy to electrical energy. More particularly, the present invention relates to an electrochemical cell having a total size or volume that is less than 0.5 cc. Such so-called miniature electrochemical cells enable numerous new and improved medical device therapies. Miniature electrochemical cells are defined as those having a size or total volume that is less than 0.5 cc.

2. Prior Art

U.S. Pat. No. 10,957,884 to Dianetti et al., which is assigned to the assignee of the present invention and incorporated herein by reference, describes a miniature electrochemical cell housed in a metallic casing having a glass-to-metal seal isolating the opposite polarity terminals. The casing consists of three main components: a lower plate supporting a cylindrically-shaped annular sidewall having an open upper end closed with a cover plate or lid. The lower plate, annular sidewall and lid are each of a metal material, for example, titanium.

The annular sidewall is selectively coated with a dielectric material to provide electrical isolation of the to-be-housed first active material, for example, an anode active material, from the metallic annular sidewall. A sealing glass is applied to the perimeter of the lower plate with the annular sidewall supported on the glass. The annular sidewall and lower plate are heated to a temperature that is sufficient to achieve a glass-to-metal seal between them. The thickness of the sealing glass combined with the glass seal bonds at the lower plate and at the dielectric material coating the annular sidewall are sufficient to ensure electrical isolation between the lower plate and the supported annular sidewall.

A layer of a first active material, for example, an anode active material, is deposited into the cavity formed by the lower plate/annular sidewall subassembly. In this position, the anode active material is in electrical contact with the exposed inner surface of the lower plate, which serves as the negative terminal for the cell, but which is electrically isolated from the annular sidewall by the above described sealing glass and dielectric material. A separator is supported on the anode active material.

Separately, a layer of a second active material, for example, a cathode active material, is contacted to an inner surface of the lid. The metallic lid/second active material subassembly is then seated on an inner step of the annular sidewall, and the lid and sidewall are welded together. In this construction, the lid connected to the annular sidewall is in electrical continuity with the cathode active material to thereby serve as the positive terminal for the cell.

Finally, the electrode assembly is activated with an electrolyte filled into the casing through a fill port in the lid. The fill port is then sealed with a closure member welded therein or by melting the material of the lid into a solid mass closing the fill port.

However, there is very limited internal space in the casing for electrolyte. In a design having the fill port centered in the lid, such as shown in the '884 patent to Dianetti et al., there simply isn't any extra internal space that can serve as an avenue for electrolyte to effectively wet the opposite polarity active materials. In addition to a lack of extra internal space, the cathode active material contacted to the inner surface of the lid substantially blocks or covers an electrolyte fill port that is centered in the casing lid.

Another vexing problem in a miniature electrochemical cell having a size or total volume that is less than 0.5 cc is that during laser welding of the lid to the annular sidewall, thermal transfer to the glass-to-metal seal that bonds the lower plate to the annular sidewall becomes challenging. When the distance from the lid/annular sidewall weld site to the glass-to-metal seal at the lower plate/annular sidewall is very small, thermal energy transfer from the welding location to the glass-to-metal seal increases the crack susceptibility of that seal.

Thus, there is a need for an improved miniature electrochemical cell that is designed to readily permit electrolyte to flow into the casing to activate the electrode assembly during the filling operation and that can be subsequently closed without compromising the cell's hermeticity.

SUMMARY OF THE INVENTION

To help ameliorate the electrolyte filling problem described above, the electrochemical cell of the present invention has the electrolyte fill port positioned close to but spaced inwardly from the annular peripheral edge of the cover plate or lid. Inside the casing, an annulus resides between the inner surface of the annular sidewall and the electrode assembly comprising a cathode current collector contacting the inner surface of the lid and the cathode active material, and the spaced apart anode active material. The electrolyte fill port is axially aligned with this annulus. The fill port axially aligned with the annulus between the electrode assembly and the casing sidewall allows the casing to be filled with electrolyte using a vacuum filling process so that activating electrolyte readily wets the anode and cathode active materials and the intermediate separator. This is especially important in the miniature electrochemical cells of the present invention having a size or total volume that is less than 0.5 cc. In such small size cells, the desired volume of electrolyte is sufficient to activate the anode and cathode active materials without there being an overabundance of electrolyte. Without the fill port being axially aligned with the annulus between the electrode assembly and casing sidewall, it is sometimes difficult for electrolyte to sufficiently wet the opposite polarity electrode active materials to promote acceptable cell discharge.

Additionally, the lid contains an embossed rim around the perimeter and around the fill port. This embossed rim is utilized during the laser welding process to absorb energy and act as a filler material into the weld joint. The energy absorption from the embossed rim helps mitigate any cracking of the glass-to-metal seal connecting the lower plate to the annular sidewall due to the relatively small size of the cell.

While the present cell designs are adapted for miniature electrochemical cells, they are also applicable to cells that have a total volume that is greater than 0.5 cc and are not classified as "miniature". Moreover, the present electrochemical cells are not limited to any one chemistry; they can be an alkaline cell, a primary lithium cell, a rechargeable lithium cell, a Ni/cadmium cell, a Ni/metal hydride cell, a supercapacitor, a thin film solid-state cell, and the like. One preferred chemistry is a lithium-ion electrochemical cell comprising a carbon-based or $Li_4Ti_5O_{12}$-based anode and a lithium metal oxide-based cathode, such as of $LiCoO_2$ or lithium nickel manganese cobalt oxide ($LiNi_aMn_bCo_{1-a-b}O_2$). The lithium-ion electrochemical cell is activated with a liquid electrolyte.

These and other aspects of the present invention will become increasingly more apparent to those skilled in the art by reference to the following detailed description and to the appended drawings.

DETAILED DESCRIPTION OF THE PREFERRED EMBODIMENTS

Figure 1:
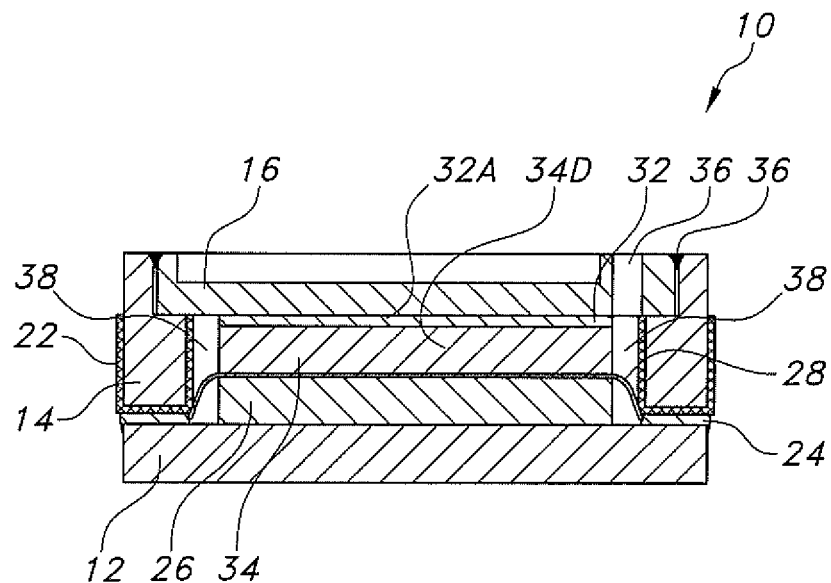
FIG. 1 is a side cross-sectional view of an electrochemical cell 10 according to the present invention.

Turning now to the drawings, FIG. 1 illustrates that an exemplary electrochemical cell 10 according to the present invention comprises an electrode assembly housed in a hermetically sealed casing. The casing comprises a lower plate 12 supporting an annular sidewall 14 having an open end closed by a plate-shaped cover or lid 16. The lower plate 12, annular sidewall 14 and lid 16 are each of a biocompatible metal, for example, titanium. In addition to titanium, suitable materials for the lower plate 12, annular sidewall 14 and lid 16 include stainless steel, mild steel, nickel-plated mild steel, but not limited thereto, so long as the metallic material is compatible for use with the other cell components.

Figure 2A:
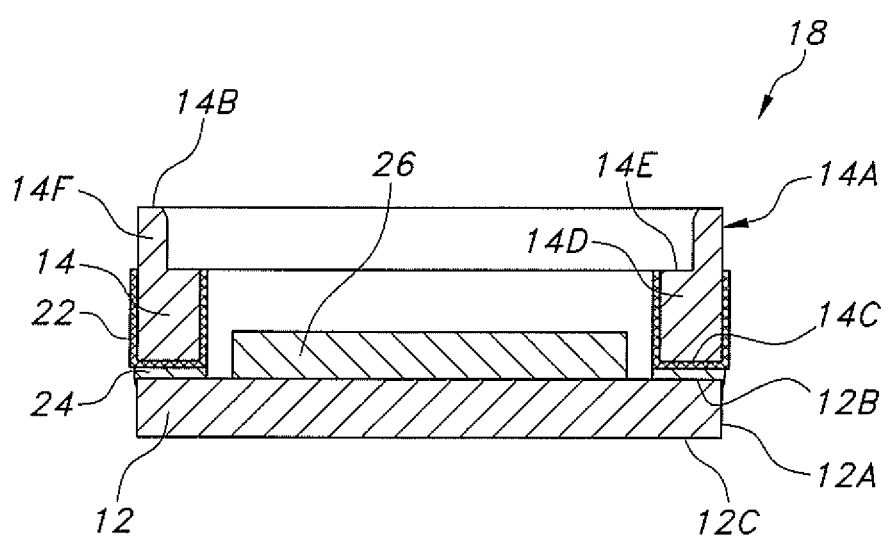
FIGS. 2A and 2B illustrate that the electrochemical cell 10 shown in FIG. 1 is assembled from a casing first or lower subassembly 18 (FIG. 2A) and a casing second or upper subassembly 20 (FIG. 2B).
Figure 2B:
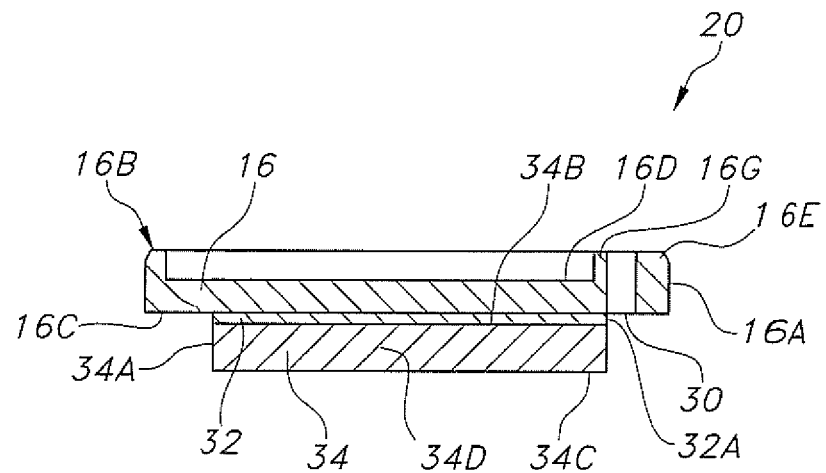
Figure 3A:
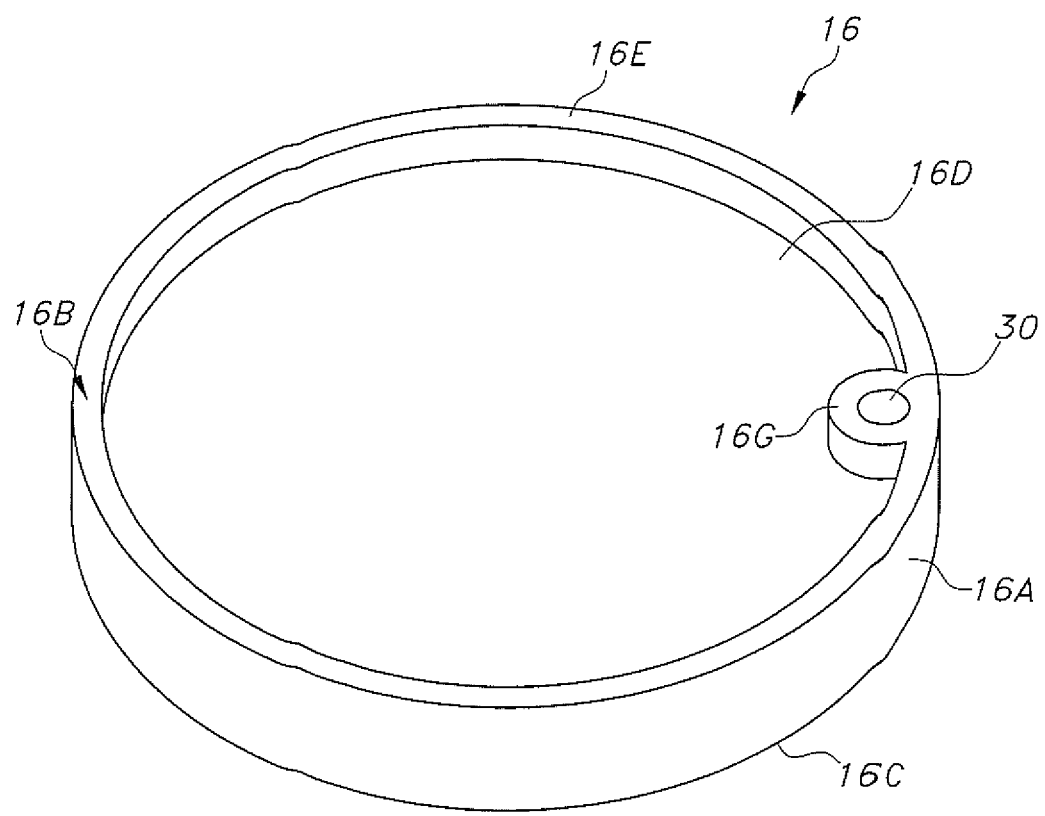
FIG. 3A is a perspective view of a lid 16 having an embossed electrolyte fill port 30 for the electrochemical cell 10 shown in FIG. 1.
Figure 3B:
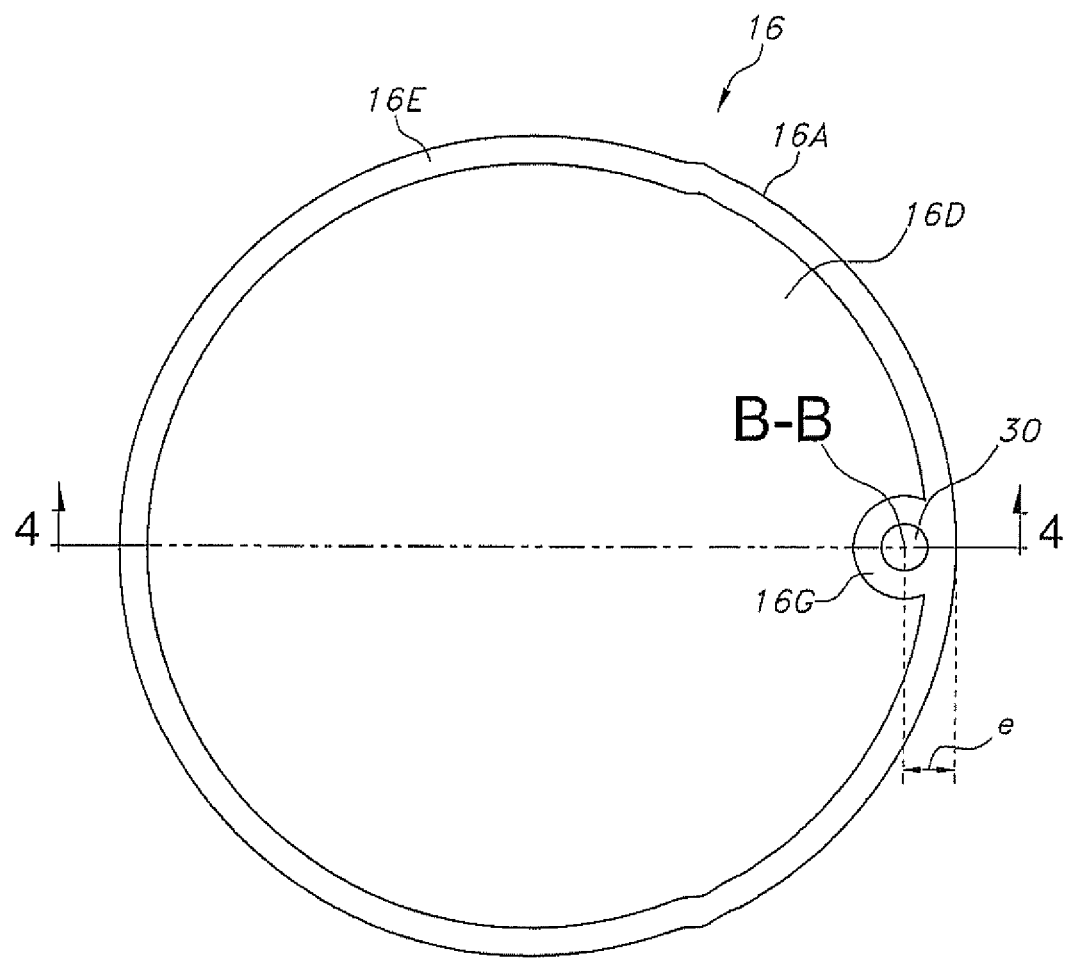
FIG. 3B is a plan view of the lid 16 shown in FIG. 3A.

FIGS. 2A and 2B illustrate that the casing for the cell 10 is assembled from a casing first or lower subassembly 18 (FIG. 2A) and a casing second or upper subassembly 20 (FIG. 2B). The casing first subassembly 18 comprises the lower plate 12 having an annular peripheral edge 12A extending to and meeting a lower plate upper surface 12B spaced from a lower plate lower surface 12C.

FIG. 2A further shows that the annular sidewall 14 comprises a cylindrically shaped outer surface 14A extending to an upper annular edge 14B spaced from a lower annular edge 14C. The upper and lower annular edges 14B, 14C reside along respective imaginary planes that are substantially parallel to each other. An inner surface of the annular sidewall 14 has a first or lower cylindrically-shaped portion 14D extending upwardly part-way along the height of the sidewall 14 from the lower annular edge 14C to a step 14E. A second or upper cylindrically-shaped portion 14F extends upwardly from the step 14E to the upper annular edge 14B.

An annular layer of dielectric material 22, for example, an alumina ($Al_2O_3$) material, is coated on the lower edge 14C and the inner surface of the lower cylindrically-shaped portion 14D of the annular sidewall 14. For ease in manufacturing, the dielectric material 22 may also be coated on the outer surface 14A. While the dielectric material 22 is shown in FIGS. 1 and 2A extending along the lower cylindrically-shaped portion 14D of the annular sidewall 14 to the step 14E, to function properly it need only extend along the inner portion 14D to a height that is greater than the thickness of the active material (either cathode or anode) that will subsequently nest in the casing lower subassembly 18.

FIGS. 1 and 2A further show that the lower plate 12 has a diameter at its annular peripheral edge 12A that is substantially similar to the outer diameter of the annular sidewall 14. To secure the lower plate 12 to the annular sidewall 14, an endless ring of sealing glass 24 is contacted or positioned on the upper planar surface 12B of the lower plate 12. The sealing glass 24 has a width that is substantially the same as and aligned with the lower edge 14C of the annular sidewall 14. Depositing the sealing glass 24 on either the lower plate 12 or the lower annular edge 14C of the annular sidewall 14 is achieved by several suitable methods including screen printing, dispensing, dipping into a frit paste or the use of a preformed endless glass ring. Suitable sealing glasses include both vitreous and crystallizing compositions that exhibit good electrical isolation properties and form mechanical bonds with good wetting characteristics to the metals of the lower plate 12 and the annular sidewall 14. Exemplary sealing glasses include, but are not limited to, Ferro IP510, Corning 1890, Schott 8422 and Schott 8629.

The lower plate 12, sealing glass 24 and annular sidewall 14 comprising the casing first subassembly 18 are then heated to a temperature that is sufficient to burn off any organic binders that may be present in the glass 24 and flow the glass into intimate contact with the dielectric material 22 contacting the lower annular edge 14C and to wick part-way up and along the height of the dielectric material coating the outer and inner surfaces of the lower cylindrically-shaped portion 140 of the sidewall 14. Upon cooling, the glass 24 forms a hermetic glass-to-metal seal between the lower plate 12 and the dielectric material coating the annular sidewall 14. The sealing glass 24 has a thickness between where it contacts the dielectric material 22 supported on the annular sidewall 14 and the facing surface of the lower plate 12 that ranges from about 0.002 inches to about 0.0025 inches, which is sufficient to ensure electrical isolation between the lower plate 12 and the annular sidewall 14.

After the lower plate 12 and the annular sidewall 14 are secured together by the intermediate sealing glass 24, a first electrode active material 26, for example, an anode active material, is supported on the upper surface 12B of the lower plate. The anode active material 26 preferably extends to an outer edge 26A that is spaced inwardly from the annular dielectric coating 22 on the inner surface of the lower cylindrically-shaped portion 14D of the annular sidewall 14. The anode active material 26 is deposited on the lower plate 12 using any one of many suitable techniques including being pressed into contact with the plate 12, preformed into a sheet that is pressed into contact with the plate 12, sprayed onto the plate 12, sputtered onto the plate 12, or coated on the plate 12. While not intending to limit the present electrochemical cell 10, the anode active material 26 has a thickness that ranges from about 5 μm to about 1 mm. In other embodiments, the anode active material 26 has a thickness that is greater than 1 mm.

Illustrative anode active materials 26 include carbon-based materials selected from coke, graphite, acetylene black, carbon black, glass carbon, hairy carbon, and mixtures thereof, or lithiated materials selected from $Li_4Ti_5O_{12}$, lithiated silver vanadium oxide, lithiated copper silver vanadium oxide, lithiated copper sulfide, lithiated iron sulfide, lithiated iron disulfide, lithiated titanium disulfide, lithiated copper vanadium oxide, $Li_xCu_wAg_yV_2O_z$ with $0.5 \leq x \leq 4.0$, $0.01 \leq w \leq 1.0$, $0.01 \leq y \leq 1.0$ and $5.01 \leq z \leq 6.5$, and mixtures thereof. Lithium is also a suitable anode active material.

A separator 28 (FIG. 1) is placed on top of the anode active material 26. The separator 28 preferably extends to the dielectric material 22 coating the inner surface of the lower cylindrically-shaped portion 14D of the annular sidewall 14. The separator 28 may also contact the sealing glass 24 supported on the lower plate 12 and has a thickness that ranges from about 5 µm to about 30 µm.

Illustrative separator materials include non-woven glass, polypropylene, polyethylene, microporous materials, glass fiber materials, ceramics, the polytetrafluorethylene membrane commercially available under the designations ZITEX (Chemplast Inc.), the polypropylene membrane commercially available under the designation CELGARD (Celanese Plastic Company Inc.) and DEXIGLAS (C. H. Dexter, Div., Dexter Corp.). Other separator materials that are useful with the present invention include woven fabrics comprising halogenated polymeric fibers, as described in U.S. Pat. No. 5,415,959 to Pyszczek et al., which is assigned to the assignee of the present invention and incorporated herein by reference. Examples of halogenated polymeric materials that are suitable for the present invention include, but are not limited to, polyethylene tetrafluoroethylene which is commercially available under the name Tefzel, a trademark of the DuPont Company, polyethylenechlorotrifluoroethylene which is commercially available under the name Halar, a trademark of the Allied Chemical Company, and polyvinylidene fluoride.

FIGS. 2B, 3A, 3B and 4 illustrate that the casing second subassembly 20 comprises the upper plate-shaped lid 16 having an annular peripheral edge 16A extending to and meeting a lid upper surface 16B spaced from a lid lower surface 16C. An inner annular recess 16D extends inwardly from the upper surface 16A part-way through the thickness of the lid 16. The lid thickness is defined as the distance "x" (FIG. 4) measured from the lid upper surface 16B to the lid lower surface 16C and ranges from about 0.0055 inches to about 0.025 inches. The annular recess 16D is spaced radially inwardly from the annular edge 16A to thereby form an annular embossed rim 16E having a height "y" measured from the lid upper surface 16B to the recess surface 16D and a width "z" measured from the lid annular peripheral edge 16A to an inner surface 16F of the rim 16E. The height "y" of the embossed rim 16E ranges from about 0.0005 inches to about 0.010 inches, and the width "z" of the rim ranges from about 0.001 inches to about 0.012 inches.

Figure 4:
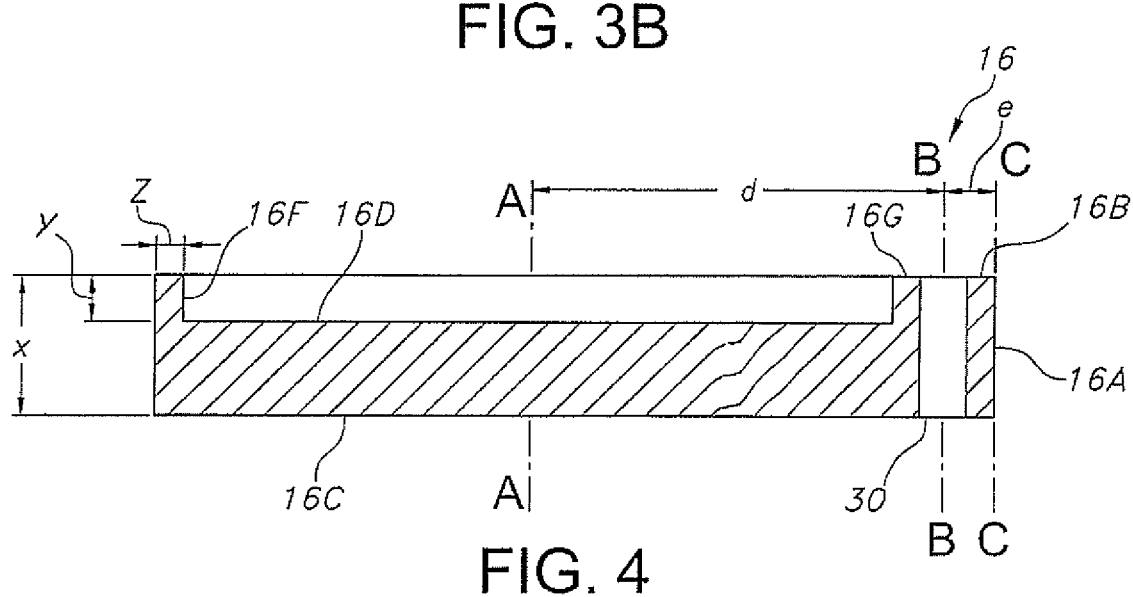
FIG. 4 is a cross-sectional view taken along line 4-4 of FIG. 3B.

An electrolyte fill opening or port 30 extends through the thickness of the lid 16 at the annular embossed rim 16E. A sleeve 16G as a portion of the lid surrounds the fill port 30. The sleeve 16G is a continuous extension of the embossed rim 16E so that the sleeve and rim together define the fill port 30. In that respect, the fill port 30 resides substantially off-center in the lid 16, spaced a relatively short distance inwardly from the annular peripheral edge 16A. As shown in FIG. 4, the lid 16 has a longitudinal axis A-A and the fill port has a longitudinal axis B-B. The distance "d" between the respective axes A-A and B-B ranges from about 0.0185 inches to about 0.30 inches. Further, the distance "e" from the longitudinal axis B-B of the fill port 30 to the closest tangent line C-C to the annular peripheral edge 16A of the lid 16 ranges from about 0.0015 inches to about 0.035 inches. Thus, the diameter of the lid 16 ranges from about 0.040 inches to about 0.67 inches and is 2× the sum of distance "d" plus distance "e". The significance of the positioning of the fill port 30 in the lid 16 will be described in greater detail hereinafter. In any event, the fill port 30 provides an open path from the upper surface 16B to the lower surface 16C of the lid 16.

Separately, a cathode current collector 32 is contacted to the lower surface 16C of the lid 16. The current collector 32 has an outer annular edge 32A that extends toward but is spaced inwardly from the electrolyte fill port 30. The current collector 32 has a thickness that ranges from about 0.1 µm to about 50 µm, and is deposited on the lower surface 16C of the lid 16 by any one of many suitable processes Including by a physical vapor deposition (PVD) process, for example, sputter deposition or evaporation deposition. Cathode current collector 32 can also be physically attached to the lid 16 by a weld. Exemplary current collector materials include nickel, titanium, copper, and Ti/NiV composites.

A second electrode active material, for example, a cathode active material 34 is contacted to the current collector 32 opposite the lid 16. That way, the exemplary cathode active material 34 is in electrical continuity with the cathode current collector 32 and the lid 16.

The cathode active material 34 has an outer annular edge 34A extending to an active material upper face 34B spaced from an active material lower face 34C. While not necessary for proper functioning of the electrochemical cell 10, the annular edge 34A is substantially aligned with the annular edge 32A of the cathode current collector 32. However, in a similar manner as with the current collector annular edge 32A, the outer annular edge 34A of the cathode active material extends toward but is spaced inwardly from the electrolyte fill port 30. That way, the annular edge 32A of the cathode current collector 32 aligned with the cathode active material 34 do not block fluid flow communication through the fill port 30 from the upper lid surface 16B to the lower surface 16C thereof and into the interior of the casing. In an exemplary embodiment, the cathode active material has a diameter of about 0.068 inches. In another exemplary embodiment, the cathode active material has a diameter that is about 0.005 inches less than the inside diameter of the annular sidewall 14.

The cathode active material 34 is deposited using any on many suitable methods (i.e. dispensed, pressed, preformed, sprayed, sputter deposition, evaporation deposition, tape casted, and as a coating). While not intending to limit the present electrochemical cell 10, the cathode active material 34 has a thickness extending to its upper and lower faces 34B, 34C that ranges from about 5 µm to about 1 mm. In other embodiments, the cathode active material 34 has a thickness that is greater than 1 mm. Suitable cathode active materials 34 are selected from $LiCoO_2$, $LiNiO_2$, $LiMnO_2$, TiS, FeS, $FeS_2$, $CF_x$, $Ag_2O$, $Ag_2O_2$, $Ag_2CrO_4$, silver vanadium oxide (SVO), copper silver vanadium oxide (CSVO), $V_2O_5$, $MnO_2$, and lithium nickel manganese cobalt oxide ($LiNi_aMn_bCo_{1-a-b}O_2$).

If desired, the cathode active material 34 is mixed with a binder material and a solvent prior to being deposited on the current collector 32. Binders such as, but not limited to, a powdered fluoro-polymer, more preferably powdered polytetrafluoroethylene or powdered polyvinylidene fluoride and solvents, such as but not limited to, trimethylphosphate (TMP), dimethylformamide (DMF), dimethylacetamide (DMAc), tetramethylurea (TMU), dimethylsulfoxide (DMSO), or n-methyl-2-pyrrolidone (NMP) may be used.

In addition, up to about 10 weight percent of a conductive diluent may be added to the cathode active material 34 to improve conductivity. Suitable materials for this purpose include acetylene black, carbon black, and graphite or, a metallic powder such as powdered nickel, aluminum, titanium, and stainless steel.

It is often the case that a current collector having an active material contacted to both of its opposed major surfaces has a plurality of openings. These openings provide the current collector with a structure like that of a screen. The openings help the opposed sheets or layers of active material lock to each other through the openings. However, in the present electrochemical cell 10, since the active material 34 only contacts the current collector 32 on one side (the side opposite the lid 16), a current collector screen is not needed. In fact, having the current collector 32 as a continuous sheet of electrically conductive material saves processing costs generally associated with providing the plurality of perforations.

The lid 16 has a diameter that is sized to fit into the second or upper cylindrically-shaped portion 14F of the annular sidewall 14, supported on the step 14E. In this seated position, the upper planar surface 16B of the lid 16 is substantially co-planar with the upper annular edge 14B of the sidewall 14. As shown in FIGS. 1 to 3, the lid 16 is hermetically secured or sealed to the sidewall 14 with an annular weld 36. In that respect, a benefit attributed to the embossed rim 16E is that it provides material that absorbs heat energy during the laser welding process and act as filler material at the weld joint.

An activating electrolyte (not shown) is then filled into the casing through the fill port 30. The fill port 30 in fluid flow communication with the annular space or annulus 38 provided between the outer annular edges 32A, 34A and 26A of the respective cathode current collector 32, cathode active material 34 and anode active material 26 and the inner surface of the lower cylindrically-shaped portion 14D of the annular sidewall or the dielectric material 22 supported on the cylindrically-shaped portion 14D allows the casing to be filled with electrolyte using a vacuum filling process.

Without this axial alignment, the electrode assembly would need to be soaked in electrolyte and the remaining casing void volume filled with additional electrolyte prior to welding the lid 16 to the annular sidewall 14. Soaking the electrode assembly in electrolyte creates multiple problems. First, internal voids within the opposite polarity electrode active materials are not optimally filled with electrolyte without a vacuum drawing electrolyte into all available porosity. A second issue relates to the difficulty in welding the lid 16 to the annular sidewall 14 in the presence of electrolyte. Heat generated by the welding process can cause electrolyte to evaporate and form out-gassing byproducts that can contaminate the weld 36, thereby reducing weld integrity.

The fill port 30 is preferably closed with a closure plug (not shown) that has been press-fit into the opening 30 defined by the sleeve 16G as a continuous extension of the embossed rim 16E. This is followed by welding the closure plug to the embossed rim 16E and sleeve 16G. Alternately, the fill port 30 is closed by directing a laser beam at the embossed rim 16E and sleeve 16G to cause the rim and sleeve to flow into and hermetically seal the port 30. Suitable closure systems for sealing an electrolyte fill port are described in U.S. Pat. No. 6,610,443 to Paulot et al., U.S. Pat. No. 7,128,765 to Paulot et al. and 10,446,825 to Voss et al. These patents are assigned to the assignee of the present invention and incorporated herein by reference.

The activating electrolyte is a nonaqueous and ionically conductive material mixture serving as a medium for migration of ions between the anode and cathode active materials during conversion of ions in atomic or molecular forms which migrate from the anode active material 26 to the cathode active material 34. Nonaqueous electrolytes that are suitable for the present electrochemical cell 10 are substantially inert to the anode and cathode active materials, and they exhibit those physical properties necessary for ionic transport, namely, low viscosity, low surface tension and wettability.

A suitable electrolyte has am inorganic, ionically conductive lithium salt dissolved in a mixture of aprotic organic solvents comprising a low viscosity solvent and a high permittivity solvent. The inorganic, ionically conductive lithium salt serves as the vehicle for migration of the anode ions to intercalate or react with the cathode active material 34. Suitable lithium salts include $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, $LiSCN$, $LiO_3SCF_3$, $LiC_6F_5SO_3$, $LiO_2CCF_3$, $LiSO_6F$, $LiB(C_6H_5)_4$ and $LiCF_3SO_3$, and mixtures thereof.

Low viscosity solvents useful with the present electrochemical cell 10 include esters, linear and cyclic ethers and dialkyl carbonates such as tetrahydrofuran (THF), methyl acetate (MA), diglyme, triglyme, tetragylme, dimethyl carbonate (DMC), 1,2-dimethoxyethane (DME), 1,2-diethoxyethane (DEE), 1-ethoxy, 2-methoxyethane (EME), ethyl methyl carbonate, methyl propyl carbonate, ethyl propyl carbonate, diethyl carbonate, dipropyl carbonate, and mixtures thereof, and high permittivity, solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GEL), N-methyl-pyrrolidinone (NMP), and mixtures thereof.

In the present electrochemical cell 10, the preferred anode active material 26 is lithium metal and the preferred electrolyte is 0.8M to 1.5M $LiAsF_6$ or $LiPF_6$ dissolved in a 30:70 mixture, by volume, of propylene carbonate as the preferred high permittivity solvent and 1,2-dimethoxyethane as the preferred low viscosity solvent.

When the present electrochemical cell 10 is of a primary chemistry, the combined thicknesses of the anode active material 26, the separator 28, the cathode active material 34 and the cathode current collector 32 is substantially equal to or slightly greater than the combined height of the sealing glass 24 and the lower inner cylindrically-shaped portion 14D of the annular sidewall 14 as measured from the lower plate 12 to the step 14E. That way, there is enough stack pressure inside the casing to provide intimate contact between the anode/cathode electrode assembly to thereby ensure acceptable discharge for the primary chemistry cell.

Alternatively, when the electrochemical cell 10 is of a secondary chemistry, the combined thicknesses of the anode active material 26, the separator 28, the cathode active material 34 and the cathode current collector 32 is somewhat less than the combined height of the sealing glass 24 and the lower inner cylindrically-shaped portion 14D of the annular sidewall 14 as measured from the lower plate 12 to the step 14E. That way, there is enough free space inside the casing to accommodate expansion and contraction of the electrode stack or anode/cathode electrode assembly as the electrochemical cell 10 of the secondary chemistry is subjected to charge and discharge cycles.

With the electrochemical cell 10 comprising the electrode assembly of the anode active material 26/cathode active material 34 activated with the electrolyte and housed inside the casing comprising the casing lower subassembly 18 (FIG. 2A) hermetically sealed to the casing upper subassembly 20 (FIG. 2B), the lid 16 welded to the annular sidewall 14 in contact with the cathode current collector 32 and the cathode active material 34 serves as the positive terminal, and the lower plate 12 in contact with the anode active material 26 serves as the negative terminal for the cell.

As those skilled in the art will readily appreciate, the cathode active material 34 can be switched with the anode active material 26. In this alternate embodiment, the cathode active material 34 in contact with cathode current collector 32 contacting the lower plate 12 serves as the positive terminal and the anode active material 26 in contact with the lid 16 welded to the annular sidewall 14 serves as the negative terminal.

With the lower plate 12 having a surface area ranging from about 1 mm$^2$ to about 1 cm$^2$ (surface area of either of the upper and lower surfaces 12B, 12O), the upper surface 16B of the lid 16 and the upper edge 14B of the annular sidewall 14 having a combined surface area ranging from about 1 mm$^2$ to about 1 cm$^2$, and with the height of the casing as measured from the lower surface 12C of the lower plate 12 to the upper edge 14B of the annular sidewall 14 ranging from about 250 µm to about 2.5 mm, the present electrochemical cell 10 represents an advancement in electrochemical technology. The cell can be built with a total volume that is less than 0.5 cc but, as a hermetically sealed enclosure, is capable of being implanted in human or animal body tissue for extended periods of time.

Thus, the purpose of the fill port 30 in fluid flow communication with the annular space 38 between the outer annular edges 32A, 34A and 26A of the respective cathode current collector 32, cathode active material 34 and anode active material 26 and the inner surface of the lower cylindrically-shaped portion 14D of the annular sidewall 14 or the inner surface of the dielectric material 22 supported on the cylindrically-shaped portion 14D provides an open pathway for electrolyte to flow downwardly past the current collector 32 to wet the cathode active material 34, the separator 28 and the anode active material 26. This is especially important in the miniature electrochemical cells of the present invention having a size or total volume that is less than 0.5 cc. In such small size cells, the desired volume of electrolyte is sufficient to activate the anode and cathode active materials 26, 34 without there being an overabundance of electrolyte. Without the above-described alignment of the fill port 30 and the internal annular space 38, it is sometimes difficult for the electrolyte to sufficiently wet the electrode assembly 26, 34 to promote acceptable cell discharge. Further, the distance "e" (FIGS. 3B and 4) from the longitudinal axis B-B of the fill port 30 to the closest tangent line C-C to the annular peripheral edge 16A of the lid ranging from about 0.0015 inches to about 0.035 inches provides sufficient lid material at the fill port 30 to ensure that when the fill port is hermetically welded shut, the lid will not be structurally compromised by the welding process, thereby ensuring long-term hermeticity for the electrochemical cell 10 of the present invention.

Further, a method for providing an electrochemical cell 10 according to the present invention comprises first providing a casing. That is done by providing a lower plate 12 and an annular sidewall 14. The annular sidewall 14 extends to an upper annular edge 14B spaced from a lower annular edge 14C, and an outer annular surface 14A spaced from an inner surface. The inner annular surface of the annular sidewall 14 is provided with a step 14E. A dielectric material 22 is coated on the lower annular edge 14C of the annular sidewall 14 and at least a portion of the inner surface of the annular sidewall. Next, a ring-shaped sealing glass 24 is contacting the lower plate 12 and the dielectric material 22 coating the lower annular edge 14C of the annular sidewall 14. This subassembly is heated to form a glass-to-metal seal between the lower plate 12 and the dielectric material 22 at the lower annular edge of the annular sidewall 14. If desired, the dielectric material 22 only coats the lower cylindrically-shaped portion 14D of the annular sidewall. That way, the sealing glass 24 seals directly to the lower plate 12 and the annular sidewall 14.

Separately, a lid 16 is provided. The lid 16 has an electrolyte fill port 30 extending through a lid thickness from a lid upper surface 16B to a spaced apart lid lower surface 16C. The lid 16 also has a recess 16D extending inwardly from the lid upper surface into its thickness. A current collector 32 is contacted to the lid lower surface 16C spaced from the electrolyte fill port 30.

An electrode assembly is then provided. The electrode assembly comprises an anode active material 26 and a cathode active material 34. One of the anode and the cathode active materials 26, 34 is contacted to the current collector 32 in turn contacting the lid 16 serving as one terminal for the cell. The other of the anode and the cathode active materials 26, 34 is contacted to the lower plate 12 serving as the other terminal for the cell. A separator 28 is positioned to segregate the anode active, material 26 from direct physical contact with the cathode active material 34.

The electrochemical cell is completed when the lid 16 is seated on the step 14E of the annular sidewall 14. The lid 16 is then welded to the upper annular edge 14B of the annular sidewall 14. Importantly, the lid 16 is provided with an embossed rim 16E extending between its outer peripheral edge 16A and the recess 16D. When the lid 16 is welded to the annular sidewall 14, the material comprising the rim 16E provides sufficient material to both absorb heat created at the weld and to provide material that flows into the gap between the lid 16 and sidewall 14 to provide a hermetic seal between these members of the casing. The heat absorbed by the rim 16E helps to prevent compromise of the glass-to-metal seal between the annular sidewall 14 and the lower plate 12.

This is followed by filling an activating electrolyte into the casing through the electrolyte fill port 30 in the lid 16 and then closing the fill port. Also, an annulus 38 resides between the inner surface of the annular sidewall 14 and the electrode assembly. The electrolyte fill port 30 is axially aligned with this annulus 38. That way, electrolyte filled into the casing through the fill port 30 readily wets the electrode assembly to thereby promote extended cell discharge.

It is appreciated that various modifications to the inventive concepts described herein may be apparent to those of ordinary skill in the art without departing from the spirit and scope of the present invention as defined by the appended claims.

What is claimed is:

1. An electrochemical cell, comprising: a) a casing, comprising: i) an annular sidewall extending to an upper annular edge spaced from a lower annular edge, The annular sidewall having an outer surface spaced from an inner surface; ii) a lid closing the upper annular edge of the annular sidewall, wherein the lid has a hermetically sealed electrolyte fill port extending from a lid upper surface to a spaced apart lid lower surface; iii) a current collector contacted to the lid lower surface; iv) a lower plate; v) a dielectric material coating the lower annular edge of the annular sidewall and at least a portion of the inner surface of the annular sidewall; and vi) a ring-shaped sealing glass in a glass-to-metal sealed relationship with the lower plate and in a hermetically sealed relationship with the dielectric material coating the lower annular edge of the annular sidewall; and b) an electrode assembly housed inside the casing, the electrode assembly comprising: i) an anode active material; ii) a cathode active material; and iii) a separator segregating the anode active material from direct physical contact with the cathode active material, iv) wherein one of the anode and the cathode active materials contacts the current collector in turn contacting the lid serving as one terminal for the cell, and the other of the anode and the cathode active materials contacts the lower plate serving as the other terminal for the cell; and c) an activating electrolyte filed in the casing to contact the electrode assembly.

2. The electrochemical cell of claim 1, wherein an annulus resides between the inner surface of the annular sidewall and the electrode assembly and the electrolyte fill port is axially aligned with the annulus.

3. The electrochemical cell of claim 1, wherein the lid has a diameter ranging from about 0.040 inches to about 0.67 inches and a longitudinal axis of the electrolyte fill port is spaced inwardly from the closest tangent line to an annular peripheral edge of the lid by a distance ranging from about 0.0015 inches to about 0.035 inches.

4. The electrochemical cell of claim 1, wherein the dielectric material is an alumina ($Al_2O_3$).

5. The electrochemical cell of claim 1, wherein the sealing glass is a vitreous and crystallizing composition.

6. The electrochemical cell of claim 1, wherein an annular peripheral edge of the lower plate has a diameter that is substantially the same as that of the outer surface of the annular sidewall.

7. The electrochemical cell of claim 1, wherein the outer surface of the annular sidewall is cylindrical.

8. The electrochemical cell of claim 1, wherein the inner surface of the annular sidewall is provided with a step, and wherein the lid is seated on the step.

9. The electrochemical cell of claim 1, wherein an upper surface of the lid is substantially co-planar with the upper annular edge of the annular sidewall.

10. The electrochemical cell of claim 1, wherein the lid is welded to the annular sidewall to thereby close the upper annular edge thereof.

11. The electrochemical cell of claim 1, wherein the electrolyte fill port is either welded closed or provided with a closure plug that is welded to the lid to hermetically seal the electrolyte fill port.

12. The electrochemical cell of claim 1, wherein a thickness of the lid measured between the lid upper and lower surfaces ranges from about 0.0055 inches to about 0.025 inches, and wherein a recess extends inwardly from the lid upper surface part-way into the thickness of the lid, the recess having a height that ranges from about 0.0005 inches to about 0.010 inches and a width that ranges from about 0.001 inches to about 0.012 inches so that with the lid closing the upper annular edge of the annular sidewall, an annular rim of the casing extends from an outer peripheral edge of the annular sidewall to the recess.

13. The electrochemical cell of claim 1, wherein the anode active material is selected from the group of coke, graphite, acetylene black, carbon black, glass carbon, hairy carbon, $Li_4Ti_5O_{12}$, lithiated silver vanadium oxide, lithiated copper silver vanadium oxide, lithiated copper sulfide, lithiated iron sulfide, lithiated iron disulfide, lithiated titanium disulfide, lithiated copper vanadium oxide, $Li_xCu_wAg_yV_2O_z$ with $0.5 \leq x \leq 4.0$, $0.01 \leq w \leq 1.0$, $0.01 \leq y \leq 1.0$ and $5.01 \leq z\ 6.5$, lithium, and mixtures thereon, and wherein the cathode active material is selected from the group of lithium nickel manganese cobalt oxide ($LiNi_aMn_bCo_{1-a-b}O_2$) $LiCoO_2$, $LiNiO_2$, $LiMnO_2$, TiS, FeS, $FeS_2$, $CF_x$, $Ag_2O$, $Ag_2O_2$, $Ag_2CrO_4$, silver vanadium oxide (SVO), copper silver vanadium oxide (CSVO), $V_2O_5$, $MnO_2$, and mixtures thereof.

14. The electrochemical cell of claim 1 having a total volume that is less than 0.5 cc.

15. An electrochemical cell, comprising: a) a casing, comprising: i) an annular sidewall extending to an upper annular edge spaced from a lower annular edge, and an outer annular surface spaced from an inner annular surface, wherein the inner annular surface of the annular sidewall is provided with a step; ii) a lid seated on the step to close the upper annular edge of the annular sidewall, wherein a lid annular peripheral edge provides a lid thickness extending to a lid upper surface spaced from a lid lower surface, and wherein a recess extends inwardly from the lid upper surface part-way into the lid thickness to thereby provide a lid annular rim that extends from the lid annular peripheral edge to the recess; iii) a hermetically sealed electrolyte fill port extending to the lid upper and lower surfaces; iv) a current collector contacted to the lid lower surface; v) a lower plate; vi) an alumina coating the lower annular edge and at least a portion of the inner surface of the annular sidewall; and vii) a ring-shaped sealing glass in a glass-to-metal sealed relationship with the lower plate and in a glass-to-ceramic sealed relationship with the alumina at the lower annular edge of the annular sidewall; and b) an electrode assembly housed inside the casing, the electrode assembly comprising: i) an anode active material; ii) a cathode active material; and iii) a separator segregating the anode active material from direct physical contact with the cathode active material, iv) wherein one of the anode and the cathode active materials contacts the current collector in turn contacting the lid serving as one terminal for the cell, and the other of the anode and the cathode active materials contacts the lower plate serving as the other terminal for the cell; and c) an activating electrolyte filled in the casing to contact the electrode assembly.

16. The electrochemical cell of claim 15, wherein an annulus resides between the inner surface of the annular sidewall and the electrode assembly and the electrolyte fill port is axially aligned with the annulus.

17. The electrochemical cell of claim 15, wherein the lid has a diameter ranging from about 0.040 inches to about 0.67 inches and a longitudinal axis of the electrolyte fill port is spaced inwardly from the closest tangent line to the annular peripheral edge of the lid by a distance ranging from about 0.0015 inches to about 0.035 inches.

18. The electrochemical cell of claim 15, wherein the annular rim of the lid is welded to the annular sidewall to thereby close the upper annular edge thereof.

19. The electrochemical cell of claim 15, wherein the sealing glass is a vitreous and crystallizing composition.

20. A method for providing an electrochemical cell, the method comprising the steps of: a) providing a casing, comprising: i) providing an annular sidewall extending to an upper annular edge spaced from a lower annular edge, and an outer annular surface spaced from an inner surface, wherein the inner annular surface is provided with a step; ii) coating a dielectric material on the lower annular edge of the annular sidewall and at least a portion of the inner surface of the annular sidewall; iii) providing a lower plate; iv) positioning a ring-shaped sealing glass contacting the lower plate and the dielectric material coating the lower annular edge of the annular sidewall; v) heating the lower plate and the annular sidewall to form a glass-to-metal seal between the lower plate and the dielectric material at the lower annular edge of the annular sidewall; vi) providing a lid; vii) providing an electrolyte fill port extending through the lid to the lid upper and lower surfaces; and viii) contacting a current collector to the lid lower surface; b) providing an electrode assembly, comprising: i) an anode active material; ii) a cathode active material; iii) contacting one of the anode and the cathode active materials to the current collector in turn contacting the lid serving as one terminal for the cell, and contacting the other of the anode and the cathode active materials to the lower plate serving as the other terminal for the cell; and iv) positioning a separator segregating the anode active material from direct physical contact with the cathode active material; c) seating the lid on the step of the annular sidewall; d) welding the lid to the upper annular edge of the annular sidewall; and e) filling an activating electrolyte into the casing through the electrolyte fill port in the lid and then closing the electrolyte fill port.

21. The method of claim 20, including providing the lid having an annular peripheral edge providing a lid thickness extending from a lid upper surface to a spaced apart lid lower surface, wherein the lid has a recess extending inwardly from the lid upper surface part-way into the thickness of the lid to thereby provide a lid annular rim extending from the lid annular peripheral edge to the lid recess, and welding the lid annular rim to the upper annular edge of the annular sidewall to thereby weld the lid to the annular sidewall.

22. The method of claim 20, including providing an annulus residing between the inner surface of the annular sidewall and the electrode assembly, wherein the electrolyte fill port is axially aligned with the annulus.

* * * * *